United States Patent [19]
Oxenkrug et al.

[11] Patent Number: 6,011,054
[45] Date of Patent: Jan. 4, 2000

[54] METHOD FOR TREATING DEPRESSION, OBSESSIVE COMPULSIVE DISORDER, AND ANXIETY WITH N—ACETYL SEROTONIN

[75] Inventors: Gregory F. Oxenkrug, Newton, Mass.; Pura J. Requintina, West Kingston, R.I.

[73] Assignee: St. Elizabeth's Medical Center of Boston, Boston, Mass.

[21] Appl. No.: 09/187,466

[22] Filed: Nov. 4, 1998

Related U.S. Application Data

[63] Continuation of application No. PCT/US98/06557, Apr. 1, 1998
[60] Provisional application No. 60/043,049, Apr. 4, 1997.
[51] Int. Cl.[7] ...................... A61K 31/405; A61K 31/535; A61K 31/445; A61K 31/44; A61K 31/135
[52] U.S. Cl. ........................ 514/415; 514/237.8; 514/321; 514/356; 514/640; 514/647; 514/649; 514/654; 514/657
[58] Field of Search ..................................... 514/415, 356, 514/649, 640, 321, 657, 654, 647, 237.8

[56] References Cited

U.S. PATENT DOCUMENTS 4,956,361 9/1990 Traber et al. .
5,552,428 9/1996 Fraschini et al. .

*Primary Examiner*—William R. A. Jarvis
*Attorney, Agent, or Firm*—David S. Resnick; Nixon Peabody LLP

[57] ABSTRACT

The present invention relates to a method of treatment of depression in a human being identified as having depression. This method comprises the administration of a therapeutically effective depression treatment amount of N-acetyl-serotonin (NAS), also referred to as N-acetyl-5-hydroxytryptamine, to a human being identified as having depression. The NAS may be administered alone or in combination with other agents, e.g., $Ca^{++}$ antagonists.

11 Claims, No Drawings

METHOD FOR TREATING DEPRESSION, OBSESSIVE COMPULSIVE DISORDER, AND ANXIETY WITH N— ACETYL SEROTONIN

This application is a continuation of PCT/US98/06557, filed Apr. 1, 1998 and claims priorty to provisional application No. 60/043,049, filed Apr. 4, 19997.

BACKGROUND OF THE INVENTION

1. Field of the Invention

The present invention relates to a method of treatment of depression in a human being identified as having depression. This method comprises the administration of a therapeutically effective depression treatment amount of N-acetylserotonin (NAS) to a human being identified as having depression. NAS may be administered alone or in combination with other agents, e.g., $Ca^{++}$ antagonists.

2. Background

Serotonin has been long ago considered to have the important role in the mechanism of antidepressant effect (see Lapin & Oxenkrug, 1969). Pineal gland has the highest concentration of serotonin in comparison with the other brain structures. Pineal serotonin is acetylated with the formation of N-acetylserotonin (NAS). NAS is further methylated by the hydroxy-indole-O-methyltransferase (HIOMT) to produce melatonin (5-methoxy-N-acetyltryptamine) (see Reiter, 1991). Melatonin exerted antidepressant-like activity in the "frog" test: potentiated the sedative effect of reserpine (Skene & Potgieter, 1981) and of selective MAO-A inhibitors (Requintina et al., 1994). We have recently observed the antidepressant-like activity of melatonin in the mouse tail suspension test (Prahie et al., in preparation). Selective MAO-A inhibitors (and some other antidepressants) stimulate the pineal NAS and melatonin production (Oxenkrug et al., 1994: see for rev. Oxenkrug, 1991). It was suggested that selective MAO-A inhibitors (and some other antidepressants) might correct the circadian rhythms abnormalities (and, thus, exert their antidepressant action) via their melatoninergic effects (Oxenkrug et al., 1986; see Oxenkrug, 1991).

Although NAS was viewed mainly only as an intermediate product of melatonin biosynthesis from serotonin, it was reported that some of its effects (i.e., hypothermic and analgesic) differed (qualitatively or quantitatively) from that of serotonin and melatonin (Morton, 1987; Psarakis et al., 1988).

DETAILED DESCRIPTION OF THE INVENTION

The present invention relates to a method of treatment of depression in a human being identified as having depression. This method comprises the administration of a therapeutically effective depression treatment amount of N-acetylserotonin (NAS), also referred to as N-acetyl-5-hydroxytryptamine, to a human being identified as having depression. The NAS may be administered alone or in combination with other agents, e.g., $Ca^{++}$ antagonists, or antidepressents, such as selective serotonin receptacle inhibitors and inhibitors of monoamine oxidase, including selective Type A and non-selective inhibitors.

Selective serotonin receptacle inhibitors include, for example, fluoxetine (Prozac®, Dista), flovoxamine (Luvox®, Solvay), paroxetine (Paxil®, Smitline Beecham), sertraline (Zoloft®, Pfizer).

Non-selective inhibitors of monoamine oxidase inhibitors include, for example, phenelzine (Nardil®, Parke-Davis), tranylcypromine (Parnate®, Smithkline Beecham).

Selective monoamine oxidase type A inhibitors include, for example, moclobemide, brofaromine and beflaxozone and others.

Depression states in which the present method is particularly useful in treating are those defined in the Diagnostic and Statistical Manual of Mental Disorders, third edition (DSM III)1, American Psychiatric Association, Washington, D.C. (1980), (DSM III, 296,2X to 296.6X and 301.13), including that characterized by anxiety or obsessional neuroses (DSM III, 300.40), or atypical depression (DSM III, 296.70 and 296.82), e.g., accompanied by a personality disorder. Other therapeutic uses for the method include treatment of post-traumatic stress disorder (DSM III, 308,30 and 309,81), obsessive compulsive behavioral states (DSM III, 300.30), anxiety states (DSM III, 300.00, 300.01, 300.02, 300.21, 300.22, 300.23 and 300.29), e.g., which are accompanied in an acute phase by panic attacks with or without phobia (DSM III 300.21), phobia (DSM III 300.23 and 300.29), appetite disorders, e.g., bulimia (DSM III, 307.51) and anorexia (DSM III, 307.10), and borderline personality disorder (DSM III, 301.83) in human beings identified as having such disorders. Still further therapeutic uses for the method include treatment of headaches, e.g., migraine, muscle contraction and mixed (i.e., combination of migraine and muscle contraction) headaches in human beings having such headaches.

NAS may be administered by, for example, the oral, rectal, transdermal, sublingual or parenteral route. In general, the compound may be administered for the treatment of each of the disorders stated hereinabove, including depression, in the dosage range of about 0.01 mg to about 500 mg per kg of human body weight per day, preferably about 0.1 mg to about 40 mg per kg of human bodyweight per day and optimally about 7 mg per kg of human bodyweight per day, although the precise dosage will naturally depend on a number of clinical factors, for example, the age of the recipient, the route of administration and the condition under treatment and its severity: for administration of NAS by the oral route, a dosage regime of 0.03 to 30 mg per kg per day, preferably 1 to 20 mg per kg per day and optimally about 7 mg per kg per day, may be used. The desired daily dose is preferably given as two or three or more subdoses administered at appropriate intervals during the day.

While it is possible to administer NAS as the raw chemical, it is highly desirable to administer it in the form of a pharmaceutical formulation comprising NAS together with an acceptable carrier therefor; the carrier should be acceptable in the sense of being compatible with the other ingredients and not deleterious to the recipient thereof. The formulations may be adapted for oral, transdermal, parenteral or rectal administration.

The formulations may conveniently be presented in unit dosage form and may be prepared by any of the methods well known in the art of pharmacy. Such methods include the step of bringing into association the active ingredient with the carrier which may comprise one or more accessory ingredients. In general the formulations are prepared by uniformly and intimately bringing into association the active ingredient with liquid carriers or finely divided solid carriers or both, and then, if necessary, shaping or encapsulating the product.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion.

A tablet may be made by compression or molding, optionally with one or more accessory ingredients. Compressed tablets may be prepared by compressing in a suitable machine the active ingredient in a free-flowing form such as a powder of granules, optionally mixed with a binder, lubricant, inert diluent, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for rectal administration may be presented as a suppository with the usual carriers such as cocoa butter.

Formulations suitable for parenteral administration include aqueous sterile injection solutions which may contain antioxidants, buffers, bacteriostats and solutes which renders the formulation isotonic with the blood of the intended recipient; and aqueous and nonaqueous sterile suspensions which may include suspending agents and thickening agents. The formulations may be presented in unit dose or multidose containers, for example sealed ampoules and vials, and may be stored in a freeze dried (lyophilized) condition requiring only the addition of the sterile liquid carrier, for example PEG 400: ethanol mixtures, immediately prior to use. Extemporaneous injection solutions and suspensions may be prepared from sterile powders, granules and tablets of the kind previously described.

Preferred unit dosage formulations are those containing a daily dose or unit daily subdose, as hereinabove recited, or an appropriate fraction thereof, of the active ingredient.

It should be understood that in addition to the ingredients particularly mentioned above the formulations of this invention may include other agents conventional in the art having regard to the type of formulation in question, for example, those suitable for oral administration may include flavoring agents.

NAS may be prepared by those methods known in the art or purchased commercially from, for example, Sigma Chemical Company.

NAS may be administered alone or in combination with other therapeutically effective agents, for example, antidepressants such as nortriptyline and MAO-inhibitors.

Additionally, the present inventors have found that, unexpectedly, the antidepressant action of NAS is potentiated by the $Ca^{++}$ antagonist Nifedipine. Accordingly NAS may be combined with a $Ca^{++}$ antagonist. Nifedipine is a preferred $Ca^{++}$ antagonist.

Inhibitors of NAS conversion into melatonin, e.g., S-odenosyihomocystein (SAM), may also be administered along with NAS to keep NAS levels at desirable levels.

The present invention is further illustrated by the following Examples. These Examples are provided to aid in the understanding of the invention and are not construed as a limitation thereof.

EXAMPLE

In order to distinguish between the effect(s) of NAS proper and the effect(s) of melatonin formed from the NAS, the tests were performed in animals that lack the ability to convert NAS into melatonin. The C57BL/6J mice are suitable animals for such a study since no enzymes of melatonin biosynthesis have been found in the pineal glands of this strain of mice (Ebihara et al., 1986). In the present study tail suspension test in C57BL/6J mice was used to evaluated NAS antidepressant-like activity.

Tail suspension test is a variant of the "behavioral despair" forced swimming test in which immobility is induced by suspending an animal by the tail (Steru et al., 1985). Unlike forced swimming, tail suspension-induced immobility is not accompanied by marked hypothermia or behavioral changes lasting longer than the test period itself, suggesting that the procedure is less stressful to the experimental animals. Although most of the clinically active antidepressants revealed antidepressant-like activity in both tests, some antidepressants are more active in tail suspension test (e.g., selective serotonin uptake inhibitors) while the other —in the forced swimming test (e.g., MAO inhibitors) (for rev. see Porsoult et al., 1993).

Considering calcium involvement in the pineal function (Morton and Reiter, 1991) and antidepressant-like activity of nifedipine, $Ca^{++}$ antagonist, demonstrated in the tail suspension test (Kozlovskii and Prahie, 1994), we have also studied the nifedipine effect on NAS-induced changes in the duration of immobility in the tail suspension test.

MATERIALS and METHODS

C57BL/6J mice (male, b.w. 21–25 g) were housed, ten per cage, in light-controlled chambers (12 hrs light/12 hrs dark cycle, lights on at 08.00, lights off at 20.00 hrs) with free access to food and water.

The chamber was 51 cmW×25 cm H×15 cmD and divided into three sections 17 cmW each. Three animals were observed simultaneously for 6 mm. Each group was composed of, at least, 9 mice (see table 1). The mouse was hung on the hook by an adhesive tape placed 15 mm from the extremity of its tail. The distance between the floor of the chamber and the nose of the animal was 10 cm.

The animals were tested (without injections) several days before the experiment. Only those animals whose duration of immobility was no less than 100 sec were selected for the further experiments.

Drugs were dissolved in saline or saline/twin (10%) or ethanol (2%) solutions and administered (i.p.) at the doses indicated in Table 1. NAS was administered 60 min before the testing, nifedipine (5 mg/kg)–30 min before the NAS. Nifedipine was used in a dose which by itself has no effect on the duration of immobility (Kozlovskii and Prahie, 1994). Results were expressed as mean+S.D.(sec).

Group differences were analyzed by the one-way ANOVA and Student's test.

RESULTS

NAS decreased duration of immobility. The effect was dose-dependent: low dose of NAS (5 mg/kg) did not affect the duration of immobility while higher doses (15, 30 and 45 mg/kg) decreased the duration of immobility, i.e., revealed the antidepressant-like activity (table 1).

Nifedipine (5 mg/kg) did not affect the duration of immobility. The combination of ineffective doses of nifedipine (5 mg/kg) and NAS (5 mg/kg) decreased the duration of immobility (table. 1).

DISCUSSION

The present results indicate that NAS has antidepressant-like activity (decreased duration of immobility) in the tail suspension test. To the best of our knowledge this is the first observation of the antidepressant-like activity of NAS. The mechanism of the NAS antidepressant-like activity revealed by the tail suspension test is unclear. This effect apparently did not depend on the NAS conversion into melatonin since no enzymes of melatonin biosynthesis have been found in the pineal glands of C57BL/6J mice used in our study (Ebihara et al., 1986). The involvement of the serotonin- 1B/D receptor was suggested in the mediation of the antidepressant-like activity in the mouse tail suspension test (O'Neill et al., 1996). In this vein, the NAS-induced change in the duration of immobility might be mediated via NAS modulating effect on serotonin receptors.

We have also found that the NAS acted synergistically with the nifedipine, $Ca^{++}$ antagonist. The possibility of the antidepressant action of nifedipine and other $Ca^{++}$ antagonists has been discussed elsewhere (Kozlovskii and Prahie, 1994). It is noteworthy that $Ca^{++}$ antagonists might increase pineal NAS levels by stimulation of serotonin-N-acetylation and inhibition of HIOMT (Morton and Reiter, 1991). However, it is unlikely that such an effect might explain the synergism of nifedipine and NAS in our study conducted on the mice lacking both enzymes of pineal melatonin biosynthesis (Ebihara et al., 1986). Further investigation of the mechanism of the NAS antidepressant-like activity and its synergism with the nifedipine is needed.

Considering that NAS is the natural compound produced by the human body and the lack of any reports of the serious side-effects from the recent wide use of NAS metabolite, melatonin, as a "food supplement", one might suggest that NAS might be applied in humans, at least, as safely as melatonin. Nifedipine is the drug that approved by the FDA for the cardiac conditions.

The following references are cited throughout the specification. All documents mentioned herein are incorporated herein by reference.

Ebihara S, Marks T, Hudson D J, M. Menaker (1986) genetic control of melatonin synthesis in the pineal gland of mouse. Science, 231: 491–493

Kozlovski V L and I V Prahie (1994) Calcium channel blockers as antidepressants—a property of the class or the individual preparation? Experimental and Clinical Pharmacology (Russian), 57: 17–20

Lapin I P, G F Oxenkrug (1969) Intensification of the central serotoninergic processes as a possible determinant of the thymoleptic effect. Lancet, 1: 32–39

Morton D J (1987) Both hydroxy- and methoxyindoles modify basal temperature in the rat. J. Pineal Res., 4:1–5

Morton D J and R J Reiter(1991) Involvement of calcium in pineal gland function. proc. Soc. Exper. Biol. Med., 197: 378–383

O'Neill M F, Fernandes A G, J M Palacios (1996) GR127935 blocks the locomotor and antidepressant-like effects of RU 24969 and the action of antidepressants in the mouse tail suspension test. Pharm. Biochem. Behav. 53:535–539

Oxenkrug (1991) The acute effect of monoamine oxidase inhibitors on serotonin conversion to melatonin. In: 5-Hydroxytryptamine and Mental Illness. Coppen A, Sandler M and Harnett S (eds). Oxford Univ. Press, pp.99–108

Oxenkrug, G. F., Balon, R., Jain, A. K., McIntyre, I. M., Appel, D. (1986) Single dose of tranylcypromine increases human plasma melatonin. Biol. Psychiat. 21:1085–1089

Oxenkrug, G., McIntyre, I., McCauley, R., and C. Filipowicz (1984). Effect of clorgyline and deprenyl on rat pineal melatonin. J. Pharm. Pharmacol. 36: 55W Poursolt R D, McArtur R A and A. Lenegre (1993) Psychotropic screening procedures. In Models in behavioral pharmacology (F. van Haaren—Ed), Elsevier Science Publishers, pp:23–50

Psarakis S, Brown G, and L I Grota (1988) Analgesia induced by N-acetylserotonin in the central nervous system, Life Sci., 42: 1109–1116

Requintina P J, Oxenkrug G F, Yuwiler A and Oxenkrug A G (1994) Synergistic sedative effect of selective MAO-A, but not MAO-B, inhibitors and melatonin in frogs. J. Neural Transm. 41(Suppl.): 141–144

Skene D and B Potgieter (1981) Investigation of two models of depression. S African J Sci, 77:180–182

Steru L, Cherwat R, Thierry B, Mico J-A, Lenegre A, Steru M, Simon P, and R D Poursolt (1987) The automated tail suspension test: a computerized device which differentiates psychotropic drugs. prog. NeuroPsychopharmacol & Biol Psychiat., 11: 659–673

Steru L, Cherwat R, Thierry B and P Simon (1985) The tail suspension test: a new method for screening antidepressants in mice. Psychopharmacology, 85:367–370.

TABLE I

N-acetyl-serotonin and Mouse Tail Suspension Test

| TREATMENT (mg/kg) | NUMBER OF ANIMALS | IMMOBILITY DURATION (sec) | P < vs. control |
|---|---|---|---|
| Control | 39 | 153.18 ± 48.11 | |
| NAS 5 | 9 | 120.00 ± 49.43 | ns |
| NAS 15 | 34 | 76.35 ± 28.57 | 0.001 |
| NAS 30 | 18 | 81.17 ± 42.35 | 0.001 |
| NAS 45 | 9 | 81.67 ± 29.23 | 0.05 |
| Nifedipine 5 | 9 | 137.35 ± 38.12 | ns |
| NAS(5) + NIF (5) | 9 | 83.67 ± 29.23 | 0.05 |

The invention has been described in detail with reference to preferred embodiments thereof However, it will be appreciated that those skilled in the art, upon consideration of this disclosure, may make modifications and improvements within the spirit and scope of the invention.

What is claimed is:

1. A method of treating depression, an obsessive compulsive disorder or anxiety in a human in need thereof which comprises administering an effective amount of N-acetyl-serotonin (NAS).

2. A method for the treatment of depression in a human being comprising the administration to said human being of an antidepressant amount of N-acetyl-serotonin (NAS).

3. The method of claim 2, wherein said NAS is administered by the oral route.

4. The method of claim 2, wherein said NAS is administered together with an acceptable carrier therefor.

5. The method of claim 2, wherein said NAS is administered in the form of an orally ingestible capsule or tablet.

6. The method of claim 2, wherein said NAS is administered in combination with a $Ca^{++}$ antagonist.

7. The method of claim 6, wherein the $Ca^{++}$ antagonist is nifedipine.

8. The method of claim 2, wherein said NAS is administered in combination with a selective serotonin uptake inhibitor or a inhibitor of monoamine oxidase.

9. The method of claim 8, wherein the selective serotonin uptake inhibitor is fluoxetine, flovoxamine, paroxetine or sertraline.

10. The method of claim 8, wherein the monoamine oxidase inhibitor is phenelzine, tranylcypromine, moclobemide, brofaromine or beflaxozone.

11. The method of claim 2, wherein said NAS is administered in combination with an inhibitor of NAS conversion into melatonin.

* * * * *